United States Patent
Morris et al.

(10) Patent No.: US 7,402,318 B2
(45) Date of Patent: *Jul. 22, 2008

(54) MEDICAL DEVICES HAVING ANTIMICROBIAL COATINGS THEREON

(75) Inventors: Carol Ann Morris, Duluth, GA (US); Manal M. Gabriel, Marietta, GA (US); Yongxing Qiu, Duluth, GA (US); Lynn Cook Winterton, Alpharetta, GA (US); John Martin Lally, Lilburn, GA (US); Marcia Kay Ash, Snellville, GA (US); Fiona Patricia Carney, Atlanta, GA (US); Courtney Flem Morgan, Alpharetta, GA (US)

(73) Assignee: Novartis AG, Basel (CH)

( * ) Notice: Subject to any disclaimer, the term of this patent is extended or adjusted under 35 U.S.C. 154(b) by 592 days.

This patent is subject to a terminal disclaimer.

(21) Appl. No.: 10/287,091

(22) Filed: Nov. 4, 2002

(65) Prior Publication Data
US 2003/0117579 A1    Jun. 26, 2003

Related U.S. Application Data

(60) Provisional application No. 60/332,289, filed on Nov. 14, 2001.

(51) Int. Cl.
*A61F 13/00*    (2006.01)
(52) U.S. Cl. .................. 424/422; 424/400; 514/772
(58) Field of Classification Search ................... None
See application file for complete search history.

(56) References Cited

U.S. PATENT DOCUMENTS

| | | | | |
|---|---|---|---|---|
| 2,271,378 A * | 1/1942 | Searle | ............... | 424/78.08 |
| 3,931,319 A | 1/1976 | Green et al. | ............... | 260/567.6 |
| 3,963,662 A | 6/1976 | Fujiwara et al. | ............... | 260/29.6 |
| 4,361,548 A * | 11/1982 | Smith et al. | ............... | 424/78.04 |
| 4,407,791 A | 10/1983 | Stark | ............... | 424/80 |
| 4,482,680 A | 11/1984 | Sheldon et al. | ............... | 525/331.4 |
| 4,525,346 A | 6/1985 | Stark | ............... | 424/80 |
| 4,621,120 A | 11/1986 | Hollister | ............... | 525/327.1 |
| 5,142,002 A | 8/1992 | Metzner | ............... | 525/540 |
| 5,256,420 A | 10/1993 | Tsao et al. | ............... | 424/427 |
| 5,328,954 A | 7/1994 | Sarangapani | ............... | 524/589 |
| 5,358,688 A | 10/1994 | Robertson | ............... | 422/28 |
| 5,515,117 A | 5/1996 | Dziabo et al. | ............... | 351/160 |
| 5,536,861 A | 7/1996 | Robertson | ............... | 556/419 |
| 5,968,538 A | 10/1999 | Snyder, Jr. | ............... | 424/404 |
| 6,051,246 A | 4/2000 | Shiau et al. | ............... | 424/409 |
| 6,107,084 A * | 8/2000 | Onda et al. | ............... | 435/289.1 |
| 6,191,192 B1 | 2/2001 | Monden et al. | ............... | 523/122 |
| 6,451,871 B1 | 9/2002 | Winterton et al. | ............... | 523/106 |
| 6,896,926 B2 * | 5/2005 | Qiu et al. | ............... | 427/2.31 |
| 6,926,965 B2 * | 8/2005 | Qiu et al. | ............... | 428/411.1 |
| 6,940,580 B2 * | 9/2005 | Winterton et al. | ............... | 351/160 H |
| 2001/0045676 A1 | 11/2001 | Winterton et al. | ............... | 264/2.5 |
| 2001/0048975 A1 | 12/2001 | Winterton et al. | ............... | 427/412.1 |

FOREIGN PATENT DOCUMENTS

| | | |
|---|---|---|
| EP | 0 604 369 A1 | 6/1994 |
| EP | 0 611 782 | 8/1994 |
| EP | 0 613 694 | 9/1998 |
| EP | 0 947 856 | 10/1999 |
| EP | 0 963 761 | 12/1999 |
| EP | 0 990 924 A1 | 4/2000 |
| WO | WO 97/05182 | 2/1997 |
| WO | WO 98/18330 | 5/1998 |
| WO | WO 99/13863 | 3/1999 |
| WO | WO 99/20258 | 4/1999 |
| WO | WO 01/92924 | 12/2001 |
| WO | WO 02/16974 | 2/2002 |

OTHER PUBLICATIONS

Composition and Method for Inhibiting of Protein on Contact Lens (Assignee—Bausch & Lomb Incorporated), Dec. 14, 2001.
Bacterial Colonization of Functionalized Polyurethanes Flemming, Capelli, Cooper and Proctor, Elsevier Science Ltd.; 1999.

* cited by examiner

*Primary Examiner*—Michael G. Hartley
*Assistant Examiner*—Eric E. Silverman
(74) *Attorney, Agent, or Firm*—Sheng-Hsin Hu; Jian Zhou

(57) ABSTRACT

The present invention provides a medical device, preferably a contact lens, which comprises an antimicrobial coating including at least one layer of polyquat of formula (I) or (II). The antimicrobial coating on the medical device of the invention has a high antimicrobial efficacy against microorganisms including Gram-positive and Gram-negative bacterial, a low toxicity, low coefficient of friction, and increased hydrophilicity while maintaining the desired bulk properties such as oxygen permeability and ion permeability of lens material. Such lenses are useful as extended-wear contact lenses. In addition, the invention provides a method for making a medical device, preferably a contact lens, having an antimicrobial coating thereon.

9 Claims, No Drawings

MEDICAL DEVICES HAVING ANTIMICROBIAL COATINGS THEREON

This application claims the benefit under 35 U.S.C. §119 (e) of United state provisional application Serial No. 60/332,289 filed Nov. 14, 2001.

The present invention generally relates to a medical device having an antimicrobial coating thereon. In particular, the present invention relates to an ophthalmic lens having an antimicrobial coating that has antimicrobial efficacy and low cytotoxicity as well as other desired properties such as low coefficient of friction, hydrophilicity, and high oxygen permeability and ion permeability. In addition, this invention provides a method for making a medical device having an antimicrobial coating.

BACKGROUND

Contact lenses are often exposed to one or more microorganisms during wear, storage and handling. They can provide surfaces onto which the microorganisms can adhere and then proliferate to form a colony. Microbial adherence to and colonization of contact lenses may enable microorganisms to proliferate and to be retained at the ocular surface for prolonged periods and thereby may cause infection or other deleterious effects on the ocular health of the eye in which the lens is used. Therefore, it is desirous to make various efforts to minimize and/or eliminate the potential for microorganism adhesion to and colonization of contact lenses.

Many attempts have been made to develop antimicrobial medical devices. Two approaches have been proposed. One approach is to incorporate antimicrobial compounds into a polymeric composition for molding a contact lens. For example, Chalkley et al. in Am. J. Ophthalmology 1966, 61:866-869, disclosed that germicidal agents were incorporated into contact lenses. U.S. Pat. No. 4,472,327 discloses that antimicrobial agents may be added to the monomer before polymerization and locked into the polymeric structure of the lens. U.S. Pat. Nos. 5,358,688 and 5,536,861 disclose that contact lenses having antimicrobial properties may be made from quaternary ammonium group containing organosilicon polymers. European patent application EP0604369 discloses that deposit-resistant contact lenses can be prepared from hydrophilic copolymers that are based on 2-hydroxyethyl methacrylate and comonomers containing a quaternary ammonium moiety. Another example is an ocular lens material, disclosed in European patent application EP0947856A2, which comprises a quaternary phosphonium group-containing polymer. A further example is U.S. Pat. No. 5,515,117 which discloses contact lenses and contact lens cases made from materials which comprise polymeric materials and effective antimicrobial components. There are some disadvantages associated with this approach for making antimicrobial contact lenses. First, polymeric compositions having antimicrobial properties may not possess all properties desired for contact lenses, especially extended-wear contact lenses, which hinders their practice uses. Second, antimicrobial compounds may exhibit greatly diminished activity since they may not in contact with microorganisms adhered to the surface of contact lens.

The other approach for making antimicrobial medical devices is to form antimicrobial coatings, containing leachable or covalently attached antimicrobial agents, on medical devices. Antimicrobial coatings containing leachable antimicrobial agents may not be able to provide antimicrobial activity over the period of time when used in the area of the human body. In contrast, antimicrobial coating containing covalently bound antimicrobial agents can provide antimicrobial activity over a relatively longer period of time. However, antimicrobial compounds in such coatings may exhibit greatly diminished activity when comparing the activity of the unbound corresponding antimicrobial compounds in solution, unless assisted by hydrolytic breakdown of either the bound antimicrobial compounds or the coating itself.

Currently, a wide variety of antimicrobial agents have been proposed to be used as coatings for contact lenses (see, for example, U.S. Pat. No. 5,328,954,). Prior known antimicrobial coatings include antibiotics, lactoferrin, metal chelating agents, substituted and unsubstituted polyhydric phenols, amino phenols, alcohols, acid and amine derivatives, and quaternary ammonium group-containing compounds. However, such antimicrobial coatings have disadvantages and are unsatisfactory. The overuse of antibiotics can lead to proliferation of antibiotic-resistant microorganisms. Other coatings may not have broad spectrum antimicrobial activity, may produce ocular toxicity or allergic reactions, or may adversely affect lens properties required for ensuring corneal health and for providing the patient with good vision and comfort.

Therefore, there is a need for antimicrobial coatings that can provide high bactericidal efficacy and broad spectrum antimicrobial activity coupled with low cytotoxicity. There is also a need for new contact lenses having antimicrobial coatings, which have high bactericidal efficacy, a broad spectrum of antimicrobial activities, and minimal adverse effects on the wearer's ocular health and comfort. Such contact lenses may have increased safety as extended-wear contact lenses which could provide comfort, convenience, and safety.

One object of the invention is to provide an antimicrobial coating which has a high antimicrobial efficacy coupled with low cytotoxicity.

Another object of the invention is to provide a medical device having an antimicrobial coating that has a high antimicrobial efficacy coupled with low cytotoxicity.

A further object of the invention is to provide a cost-effective and efficient process for forming an antimicrobial coating on a medical device.

SUMMARY OF THE INVENTION

These and other objects of the invention are met by the various aspects of the invention described herein.

The invention, in one aspect, provides a medical device having an antimicrobial surface coating and the following surface properties: a low coefficient of friction characterized by having an averaged value of less than 1.4 and a hydrophilicity characterized by having an averaged contact angle of less than 80 degree. The antimicrobial coating preferably comprises at least one layer of polymeric quaternary ammonium group-containing compound (polyquats) and has a balance of high antimicrobial efficacy and low cytotoxicity.

The invention, in another aspect, provides a method for forming an antimicrobial coating on a medical device. The method comprises applying at least one layer of polymeric quaternary ammonium group-containing compound on a medical device.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF THE PREFERRED EMBODIMENTS

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings.

An "article" refers to an ophthalmic lens, a mold for making an ophthalmic lens, or a medical device other than ophthalmic lens.

A "medical device", as used herein, refers to a device having surfaces that contact tissue, blood, or other bodily fluids of patients in the course of their operation or utility. Exemplary medical devices include: (1) extracorporeal devices for use in surgery such as blood oxygenators, blood pumps, blood sensors, tubing used to carry blood and the like which contact blood which is then returned to the patient; (2) prostheses implanted in a human or animal body such as vascular grafts, stents, pacemaker leads, heart valves, and the like that are implanted in blood vessels or in the heart; (3) devices for temporary intravascular use such as catheters, guide wires, and the like which are placed into blood vessels or the heart for purposes of monitoring or repair; and (4) ophthalmic lenses. In a preferred embodiment, medical devices are ophthalmic lenses.

An "ophthalmic lens", as used herein, refers to any lens intended for use in intimate contact with the eye of the user. This includes, without limitation, intraocular lenses, ocular implants, hard contact lenses, soft contact lenses, and corneal onlays.

The "outer surface" of a lens, as used herein, refers to the surface of the lens which faces away from the eye during wear. The outer surface, which is typically substantially convex, may also be referred to as the front curve of the lens. The "inner surface" of a lens, as used herein, refers to the surface of the lens which faces towards the eye during wear. The inner surface, which is typically substantially concave, may also be referred to as the base curve of the lens.

"Ophthalmically compatible", as used herein, refers to a material or surface of a material which may be in intimate contact with the ocular environment for an extended period of time without significantly damaging the ocular environment and without significant user discomfort. Thus, an ophthalmically compatible contact lens will not produce significant corneal swelling, will adequately move on the eye with blinking to promote adequate tear exchange, will not have substantial amounts of protein or lipid adsorption, and will not cause substantial wearer discomfort during the prescribed period of wear.

"Ocular environment", as used herein, refers to ocular fluids (e.g., tear fluid) and ocular tissue (e.g., the cornea) which may come into intimate contact with a contact lens used for vision correction, drug delivery, wound healing, eye color modification, or other ophthalmic applications.

A "monomer" means a low molecular weight compound that can be polymerized. Low molecular weight typically means average molecular weights less than 700 Daltons.

A "macromer" refers to medium and high molecular weight compounds or polymers that contain functional groups capable of further polymerization. Medium and high molecular weight typically means average molecular weights greater than 700 Daltons.

"Polymer" means a material formed by polymerizing one or more monomers.

"Surface modification", as used herein, refers to treating an article to alter its surface properties. For example, the surface modification of a contact lens includes, without limitation, the grafting of monomers or macromers onto polymers to make the lens biocompatible, deposit resistant, more hydrophilic, more hydrophobic, or the deposing of polyionic materials (LbL coating) to increase the lens hydrophilic properties or to impart antimicrobial or antifungal properties.

"LbL coating", as used herein, refers to a coating which is obtained by layer-by-layer ("LbL") deposition of polyelectrolytes on an article. The LbL coating of an article is not covalently attached to the surface of the article. Any suitable LbL polyelectrolyte deposition techniques can be used in the LbL coating. For example, a pending U.S. patent application Ser. No. 09/199,609, filed on Nov. 25, 1998, discloses an LbL polyelectrolyte deposition technique that involves consecutively dipping a substrate into oppositely charged polyionic materials until a coating of a desired thickness is formed.

As used herein, "asymmetrical coatings" on an ophthalmic lens refers to the different coatings on the first surface and the opposite second surface of the ophthalmic lens. As used herein, "different coatings" refers to two coatings that have different surface properties or functionalities.

A "capping layer", as used herein, refers to the last layer of a coating material which is applied onto the surface of a medical device.

A "polyquat", as used herein, refers to a polymeric quaternary ammonium group-containing compound.

As used herein, a "polyionic material" refers to a polymeric material that has a plurality of charged groups, such as polyelectrolytes, p- and n-type doped conducting polymers. Polyionic materials include both polycationic (having positive charges) and polyanionic (having negative charges) materials.

An "antimicrobial coating", as used herein, refers to a coating that impart to a medical device the ability to decrease or eliminate or inhibit the growth of microorganisms on the surface of the medical device.

An "antimicrobial agent", as used herein, refers to a chemical that is capable of decreasing or eliminating or inhibiting the growth of microorganisms such as that term is known in the art.

The "oxygen transmissibility" of a lens, as used herein, is the rate at which oxygen will pass through a specific ophthalmic lens. Oxygen transmissibility, Dk/t, is conventionally expressed in units of barrers/mm, where t is the average thickness of the material [in units of mm] over the area being measured and "barrer/mm" is defined as:

$$[(cm^3\ oxygen)/(cm^2)(sec)(mm^2\ Hg)] \times 10^{-9}$$

The "oxygen permeability", Dk, of a lens material does not depend on lens thickness. Oxygen permeability is the rate at which oxygen will pass through a material. Oxygen permeability is conventionally expressed in units of barrers, where "barrer" is defined as:

$$[(cm^3\ oxygen)(mm)/(cm^2)(sec)(mm^2\ Hg)] \times 10^{-10}$$

These are the units commonly used in the art. Thus, in order to be consistent with the use in the art, the unit "barrer" will have the meanings as defined above. For example, a lens having a Dk of 90 barrers ("oxygen permeability barrers") and a thickness of 90 microns (0.090 mm) would have a Dk/t of 100 barrers/mm (oxygen transmissibility barrers/mm).

The "ion permeability" through a lens correlates with both the Ionoflux Diffusion Coefficient and the Ionoton Ion Permeability Coefficient.

The Ionoflux Diffusion Coefficient, D, is determined by applying Fick's law as follows:

$$D = -n'/(A \times dc/dx)$$

where
- n'=rate of ion transport [mol/min]
- A=area of lens exposed [mm$^2$]
- D=Ionoflux Diffusion Coefficient[mm$^2$/min]
- dc=concentration difference [mol/L]
- dx=thickness of lens [mm]

The Ionoton Ion Permeability Coefficient, P, is then determined in accordance with the following equation:

$$\ln(1-2C(t)/C(0)) = -2APt/Vd$$

where:
- C(t)=concentration of sodium ions at time t in the receiving cell
- C(0)=initial concentration of sodium ions in donor cell
- A=membrane area, i.e., lens area exposed to cells
- V=volume of cell compartment (3.0 ml)
- d=average lens thickness in the area exposed
- P=permeability coefficient An Ionoflux Diffusion Coefficient, D, of greater than about $0.2 \times 10^{-3}$ mm$^2$/min is preferred, while greater than about $0.64 \times 10^{-3}$ mm$^2$/min is more preferred and greater than about $1.0 \times 10^{-3}$ mm$^2$/min is most preferred.

An "averaged value of coefficient of friction" refers to a value of coefficient of friction, which is obtained by averaging measurements of at least 3 individual medical devices.

An "averaged contact angle" refers to a contact angle (Sessile Drop), which is obtained by averaging measurements of at least 3 individual medical devices.

In general, the present invention is directed to a medical device having a core material and an antimicrobial surface coating (hereinafter antimicrobial coating) formed thereon and the following surface properties: a low coefficient of friction characterized by having an averaged value of less than 1.4 and a hydrophilicity characterized by having an averaged contact angle of less than 80 degree. The antimicrobial coating can comprise any known suitable antimicrobial agents. Exemplary antimicrobial agents include, without limitation, antibiotics, lactoferrin, metal chelating agents, substituted and unsubstituted polyhydric phenols, amino phenols, alcohols, acid and amine derivatives, and quaternary ammonium group-containing compounds. Antimicrobial agents in the antimicrobial coating of a medical device can be covalent bound to or entrapped to the medical device.

In particular, the present invention is directed to a medical device, preferably an ophthalmic lens, more preferably a contact lens, having an antimicrobial coating comprising at least one layer, preferably one capping layer, of polymeric quaternary ammonium salt compounds or the like. Surprisingly, it has been discovered that a previously known polymeric quaternary ammonium salt compound (polyquat) of formula (I) or (II)

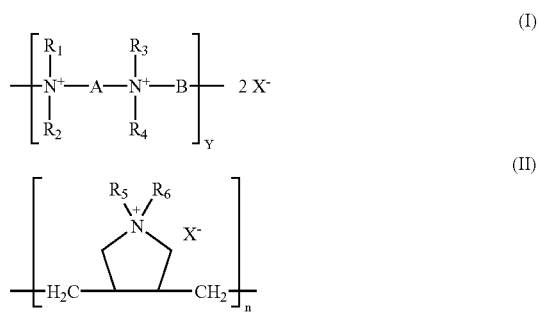

can be used to form on a contact lens an antimicrobial coating having a high antimicrobial efficacy and low cytotoxicity. Especially, when such antimicrobial coating is formed on a contact lens which is made from ophthalmically compatible materials, for example, materials disclosed in U.S. Pat. No. 5,849,811, it provides high antimicrobial activity coupled with low cytotoxicity, increases surface hydrophilicity, decreases coefficient of friction, and has a minimal adverse effects on the desirable bulk properties of the lens, such as oxygen permeability, ion permeability, and optical properties. Coefficient of friction may be one of important parameters that may affect the on-eye movement and thereby the wearer's comfort. High coefficient of friction may increase the likelihood of damaging mechanically the ocular epithelia and/or may lead to ocular discomfort. An antimicrobial coating of the present invention may find particular use in extended-wear contact lenses.

In formula (I), $R_1$, $R_2$, $R_3$ and $R_4$ are identical or different from one another. They are $C_1$-$C_{10}$ hydrocarbon radicals, preferably $C_1$ to $C_6$ alkyl radicals or $C_1$ to $C_6$ alkyl radicals having one or more hydroxyl groups, more preferably methyl, ethyl, or benzyl radicals, even more preferably methyl radicals.

In formula (I), A and B are identical or different from one another. They are n-alkylene groups having 3 to 15 carbon atoms or n-alkylene groups having 3 to 15 carbon atoms and one or more hydroxyl groups. Preferably, either one of A and B is hexamethylene radical (—CH$_2$CH$_2$CH$_2$CH$_2$CH$_2$CH$_2$—). More preferably, either one of A and B is hexamethylene radical (—CH$_2$CH$_2$CH$_2$CH$_2$CH$_2$CH$_2$—) and the respective other one is an n-alkylene group having 6 to 10 carbon atoms. Even more preferably, either one of A and B is hexamethylene radical (—CH$_2$CH$_2$CH$_2$CH$_2$CH$_2$CH$_2$—) and the respective other one is an n-alkylene group having 8 to 10 carbon atoms.

Where either one of A and B is hexamethylene radical (—CH$_2$CH$_2$CH$_2$CH$_2$CH$_2$CH$_2$—) and the respective other one is an n-alkylene radical having 6 to 12 carbon atoms, the polyquat of formula (I) will be represented by PQ6-x, in which x represents the number of carbon atoms of n-alkylene radical.

It is possible as well to provide the polymer chains with varying proportions of alkylene groups of different lengths. For example, one of A and B may be hexamethylene radical (—CH$_2$CH$_2$CH$_2$CH$_2$CH$_2$CH$_2$—), while the respective other one is n-alkylene radical having 6, 8, 10, or 12 carbon atoms, and these being present in different proportions. It is possible, for example, to produce polymers which contain 80% of hexamethylene units and 10% each of decamethylene and dodecamethylene groups. Depending on the starting material used, these different alkylene groups may be distributed statistically or in a more or less orderly fashion throughout the polymer chain.

In formula (I), the index y characterizes the chain length of the polymer of formula (I) and is a number from about 10 to 500, preferably a number from 25 to 400, and more preferably a number from 50 to 300. X is chlorine, bromine, or iodine.

In formula (II), X is chlorine, bromine, or iodine. The index n characterizes the chain length of the polymer of formula (II) and is a number from about 100 to 5000, preferably a number from 500 to 4000, and more preferably a number from 500 to 3000. $R_5$ and $R_6$ are identical or different from one another. They are n-alkyl groups having 1 to 10 carbon atoms or n-alkyl groups having 1 to 10 carbon atoms and one or more hydroxyl groups. Preferably, $R_5$ and $R_6$ are identical and methyl groups.

Methods for making a polymer of formula (I) are well known in the art. Reference is made in this context to U.S. Pat. Nos. 2,261,002, 2,271,378 and 3,898,188. Generally, a polymer of formula (I) can be synthesized by reacting a diamine having of formula (III)

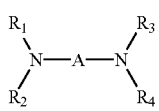

(III)

with a dihalide of formula XBX, in which $R_1$, $R_2$, $R_3$, $R_4$, A, B, and X are as defined above.

It has also been discovered that an unleachable antimicrobial coating can be formed on a medical device made from a core material by covalently attaching at least one layer of polymers of polyquat of formula (I) to the surface of the medical device or by non-covalently applying at least one layer of polyquat of formula (I) onto the surface of the medical device using a layer-by-layer polyelectrolyte deposition technique. The antimicrobial activity of the polyquat of formula (I) is not diminished significantly in the antimicrobial coating formed on the medical device.

In a preferred embodiment, a medical device of the invention comprises a core material and an antimicrobial LbL coating including at least one polyquat-polyanionic bilayer which is composed of one layer of a polyanionic material and one layer of polyquat of formula (I) or (II). In a more preferred embodiment, the medical device of the invention further comprises a plurality of polyelectrolyte bilayers. A polyelectrolyte bilayer is composed of a first layer of a first polyionic material and a second layer of a second polyionic material having charges opposite of the charges of the first polyionic material.

A polycationic material used in the present invention can generally include any material known in the art to have a plurality of positively charged groups along a polymer chain. For instance, suitable examples of such polycationic materials can include, but are not limited to, poly(allylamine hydrochloride) (PAH), poly(ethyleneimine) (PEI), poly(vinylbenzyltriamethylamine) (PVBT), polyaniline (PAN or PANI) (p-type doped) [or sulphonated polyaniline], polypyrrole (PPY) (p-typed doped), and poly(pyridinium acetylene).

A polyanionic material used in the present invention can generally include any material known in the art to have a plurality of negatively charged groups along a polymer chain. For example, suitable polyanionic materials can include, but are not limited to, polymethacrylic acid (PMA), polyacrylic acid (PAA), poly(thiophene-3-acetic acid) (PTAA), poly(4-styrenesulfonic acid) (PSS), sodium poly(styrene sulfonate) (SPS) and poly(sodium styrene sulfonate) (PSSS).

The foregoing lists are intended to be exemplary, but clearly are not exhaustive. A person skilled in the art, given the disclosure and teaching herein, would be able to select a number of other useful polyionic materials.

In order to alter various characteristics of the coating, such as thickness, the molecular weight of the polyionic materials including polyquats can be varied. In particular, as the molecular weight is increased, the coating thickness generally increases. However, if the increase in molecular weight increase is too substantial, the difficulty in handling may also increase. As such, polyionic materials used in a process of the present invention will typically have a molecular weight $M_n$ of about 2,000 to about 150,000. In some embodiments, the molecular weight is about 5,000 to about 100,000, and in other embodiments, from about 75,000 to about 100,000.

In another preferred embodiment, a medical device of the invention comprises a core material and an antimicrobial LbL coating including a capping layer of polyquat of formula (I) or (II). With such capping layer of polyquat of formula (I) or (II), an antimicrobial coating on a medical device of the invention can provide a direct contact with the antimicrobial agents, polyquat of formula (I) or (II) for microorganisms and thereby have a higher antimicrobial efficacy.

In another preferred embodiment, a medical device of the invention comprises a core material and an antimicrobial LbL coating including a plurality of layers of polyquat of formula (I) or (II). Such antimicrobial coating may provide higher concentration of antimicrobial agents and thereby increase antimicrobial efficacy.

In accordance with the present invention, the core material of a medical device may be any of a wide variety of polymeric materials. Exemplary core materials include, but are not limited to, hydrogels, silicone-containing hydrogels, polymers and copolymers of styrene and substituted styrenes, ethylene, propylene, acrylates and methacrylates, N-vinyl lactams, acrylamides and methacrylamides, acrylonitrile, acrylic and methacrylic acids. A preferred group of polymeric materials forming ophthalmic lenses are those materials which are highly oxygen permeable, such as fluorine- or siloxane-containing polymers. In particular, the polymeric materials described in U.S. Pat. No. 5,760,100 are an exemplary group, and the teachings of this patent are incorporated herein by reference.

One embodiment of the invention is a method for producing a medical device having a core material and an antimicrobial coating including a capping layer of polyquats of formula (I) or (II), comprising covalently coupling the polyquats of formula (I) or (II) to the core material.

Any known suitable method for covalent coupling of polyquats to the core material can be used. For example, a contact lens made from a hydrogel, such as lotrafilcon A, lotrafilcon B, or balafilcon, is dipped into or sprayed with a solution containing a diaziridine compound, which is subsequently attached covalently to the surface of the contact lens via a thermal process, so as to functionalize the contact lens. Such functionalized lenses can be placed in a container containing a polyquat solution and then irradiated with blue light for 30 minutes so that polyquats are covalently attached to the functionalized lens.

It should be understood that the surface of the medical device can be chemically modified before covalently coupling polyquats to the medical device or a different material can be first grafted onto or bound to the core material and then covalently coupled with polyquats.

Another embodiment of the invention is a method for producing a medical device having a core material and an antimicrobial LbL coating including a capping layer of polyquats of formula (I) or (II) comprising applying the antimicrobial LbL coating onto the core material using a layer-by-layer polyelectrolyte deposition technique.

It has been discovered and disclosed in U.S. application Ser. No. 09/005,317 that complex and time-consuming pretreatment of a core material (medical device) is not required prior to non-covalently binding of a polyionic material to the core material. By simply contacting a core material of a medical device, for example, a contact lens, with one or more solutions each containing one or more polyionic materials, an LbL coating can be formed on a medical device to modify the surface properties of the core material of the medical device. An LbL coating can be a single layer or a bilayer or multiple bilayers.

Application of an LbL coating may be accomplished in a number of ways as described in pending U.S. patent application (application Ser. Nos. 09/005,317, 09/774,942, 09/775,104), herein incorporated by reference in their entireties. One coating process embodiment involves solely dip-coating and dip-rinsing steps. Another coating process embodiment involves solely spray-coating and spray-rinsing steps. However, a number of alternatives involve various combinations of spray- and dip-coating and rinsing steps may be designed by a person having ordinary skill in the art.

One dip-coating alternative involves the steps of applying a coating of a first polyionic material to a core material of a medical device by immersing said medical device in a first solution of a first polyionic material; rinsing the medical device by immersing the medical device in a rinsing solution; and, optionally, drying the medical device. This procedure can be repeated using a second polyionic material, with the second polyionic material having charges opposite of the charges of the first polyionic material, in order to form a polyionic bilayer. This bilayer formation process may be repeated a plurality of times in order to produce a thicker LbL coating. A preferred number of bilayers is about 5 to about 20 bilayers. While more than 20 bilayers are possible, it has been found that delamination may occur in some LbL coatings having an excessive number of bilayers.

The immersion time for each of the coating and rinsing steps may vary depending on a number of factors. Preferably, immersion of the core material into the polyionic solution occurs over a period of about 1 to 30 minutes, more preferably about 2 to 20 minutes, and most preferably about 1 to 5 minutes. Rinsing may be accomplished in one step, but a plurality of rinsing steps can be quite efficient.

Another embodiment of the coating process is a single dip-coating process as described in U.S. application Ser. No. 09 775104, herein incorporated by reference in its entirety. Such single dip-coating process involves dipping a core material of a medical device in a solution containing a negatively charged polyionic material and a positively charged polyionic material in an amount such that the molar charge ratio of said solution is from about 3:1 to about 100:1. Multiple bilayers can be formed on a medical device by using this single dip-coating process.

Another embodiment of the coating process involves a series of spray coating techniques. The process generally includes the steps of applying a coating of a first polyionic material to a core material of a medical device with a first solution of a first polyionic material; rinsing the medical device by spraying the medical device with a rinsing solution; and optionally, drying the medical device. Similar to the dip-coating process, the spray-coating process may be repeated with a second polyionic material, with the second polyionic material having charges opposite of the charges of the first polyionic material.

The contacting of the medical device with solution, either polyionic material or rinsing solution, may occur by a variety of methods. For example, the medical device may be dipped into both solutions. One preferred alternative is to apply the solutions in a spray or mist form. Of course, various combinations may be envisioned, e.g., dipping the medical device in the polyionic material followed by spraying the rinsing solution.

The spray coating application may be accomplished via a number of methods. For example, a conventional spray coating arrangement may be used, i.e., the liquid material is sprayed by application of fluid, which may or may not be at elevated pressure, through a reduced diameter nozzle which is directed towards the deposition target.

Preferably, a spraying process is selected from the group consisting of an air-assisted atomization and dispensing process, an ultrasonic-assisted atomization and dispensing process, a piezoelectric assisted atomization and dispensing process, an electro-mechanical jet printing process, a piezoelectric jet printing process, a piezo-electric with hydrostatic pressure jet printing process, and a thermal jet printing process; and a computer system capable of controlling the positioning of the dispensing head of the spraying device on the ophthalmic lens and dispensing the coating liquid. Those spraying coating processes are described in U.S. Application No. 60/312,199, herein incorporated by reference in its entirety. By using such spraying coating processes, an asymmetrical coating can be applied to a medical device. For example, the back surface of a contact lens can be coated with a hydrophilic and/or lubricous coating material and the front surface of the contact lens can be coated with an antimicrobial material. It is also possible to produce a coating on a contact lens, the coating having a functional pattern so as to provide simultaneously multiple benefits to a wearer.

In accordance with the present invention, polyionic material solutions can be prepared in a variety of ways. In particular, a polyionic solution of the present invention can be formed by dissolving the polyionic material(s) in water or any other solvent capable of dissolving the materials. When a solvent is used, any solvent that can allow the components within the solution to remain stable in water is suitable. For example, an alcohol-based solvent can be used. Suitable alcohols can include, but are not limited to, isopropyl alcohol, hexanol, ethanol, etc. It should be understood that other solvents commonly used in the art can also be suitably used in the present invention.

Whether dissolved in water or in a solvent, the concentration of a polyionic material in a solution of the present invention can generally vary depending on the particular materials being utilized, the desired coating thickness, and a number of other factors. However, it may be typical to formulate a relatively dilute aqueous solution of polyionic material. For example, a polyionic material concentration can be between about 0.001% to about 0.25% by weight, between about 0.005% to about 0.10% by weight, or between about 0.01% to about 0.05% by weight.

In general, the polyionic solutions mentioned above can be prepared by any method well known in the art for preparing solutions. For example, in one embodiment, a polyanionic solution can be prepared by dissolving a suitable amount of the polyanionic material, such as polyacrylic acid having a molecular weight of about 90,000, in water such that a solution having a certain concentration is formed. In one embodiment, the resulting solution is a 0.001 M PAA solution. Once dissolved, the pH of the polyanionic solution can also be adjusted by adding a basic or acidic material. In the embodiment above, for example, a suitable amount of 1 N hydrochloric acid (HCl) can be added to adjust the pH to 2.5.

Polycationic solutions can also be formed in a manner as described above. For example, in one embodiment, poly(allylamine hydrochloride) having a molecular weight of about 50,000 to about 65,000 can be dissolved in water to form a 0.001 M PAH solution. Thereafter, the pH can also be adjusted to 2.5 by adding a suitable amount of hydrochloric acid.

In some embodiments of the present invention, it may be desirable to apply a solution containing both polyanionic and polycationic materials within a single solution. For example, a polyanionic solution can be formed as described above, and then mixed with a polycationic solution that is also formed as described above. In one embodiment, the solutions can then be mixed slowly to form the coating solution. The amount of each solution applied to the mix depends on the molar charge ratio desired. For example, if a 10:1 (polyanion:polycation) solution is desired, 1 part (by volume) of the PAH solution can be mixed into 10 parts of the PAA solution. After mixing, the solution can also be filtered if desired.

A medical device of the invention can also be made by first applying an antimicrobial coating to a mold for making a medical device and then transfer-grafting the antimicrobial coating to the medical device made from the mold, in substantial accordance with the teachings of U.S. patent application (Ser. No. 09/774,942), herein incorporated by reference in its entirety.

Methods of forming mold sections for cast-molding a contact lens are generally well known to those of ordinary skill in the art. The process of the present invention is not limited to any particular method of forming a mold. In fact, any method of forming a mold can be used in the present invention. However, for illustrative purposes, the following discussion has been provided as one embodiment of forming a mold on which a color image can be printed in accordance with the present invention.

In general, a mold comprises at least two mold sections (or portions) or mold halves, i.e. first and second mold halves. The first mold half defines a first optical surface and the second mold half defines a second optical surface. The first and second mold halves are configured to receive each other such that a contact lens forming cavity is formed between the first optical surface and the second optical surface. The first and second mold halves can be formed through various techniques, such as injection molding. These half sections can later be joined together such that a contact lens-forming cavity is formed therebetween. Thereafter, a contact lens can be formed within the contact lens-forming cavity using various processing techniques, such as ultraviolet curing.

Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S. Pat. No. 5,894,002 to Boneberger et al., which are also incorporated herein by reference.

Virtually all materials known in the art for making molds can be used to make molds for making contact lenses. For example, polymeric materials, such as polyethylene, polypropylene, and PMMA can be used. Other materials that allow UV light transmission could be used, such as. quartz glass.

Once a mold is formed, a transferable antimicrobial LbL coating, which comprises at least one layer of polyquat of formula (I) or (II), can be applied onto the optical surface (inner surface) of one or both mold portions by using the above-described LbL deposition techniques. The inner surface of a mold portion is the cavity-forming surface of the mold and in direct contact with lens-forming material. A transferable antimicrobial LbL coating can be applied onto the mold portion defining the posterior (concave) surface of a contact lens or on the mold section defining the anterior surface of a contact lens or on both mold portions.

Once a transferable antimicrobial LbL coating is applied onto the optical surface of one or both mold portions, a lens material can then be dispensed into the contact lens forming cavity defined by the assembled mold halves. In general, a lens material can be made from any polymerizable composition. In particular, when forming a contact lens, the lens material may be an oxygen-permeable material, such as flourine- or siloxane-containing polymer. For example, some examples of suitable substrate materials include, but are not limited to, the polymeric materials disclosed in U.S. Pat. No. 5,760,100 to Nicolson et al., which is incorporated herein by reference. The lens material can then be cured, i.e. polymerized, within the contact lens-forming cavity to form the contact lens, whereby at least a portion of the transferable coating detaches from the optical surface and reattaches to the formed contact lens.

Thermal curing or photo curing methods can be used to curing a polymerizable composition in a mold to form an ophthalmic lens. Such curing methods are well-known to a person skilled in the art.

The previous disclosure will enable one having ordinary skill in the art to practice the invention. In order to better enable the reader to understand specific embodiments and the advantages thereof, reference to the following examples is suggested.

EXAMPLE 1

Preparation of Coating Solutions

Polyacrylic Acid (PAA) Solution

A solution of polyacrylic acid (PAA) having an averaged molecular weight of about 90,000 is prepared by dissolving a suitable amount of PAA in water to have [PAA]=0.001 M. PAA concentration is calculated based on the repeating unit in PAA. Once dissolved, the pH of the PAA solution is adjusted to a desired value.

Poly(Allylamine Hydrochloride) (PAH) Solution

A solution of poly(allylamine hydrochloride) (PAH) having an averaged molecular weight of about 60,000 is prepared by dissolving a suitable amount of the material in water to form a 0.001 M PAH solution. PAH concentration is calculated based on the repeating unit in PAH. Once dissolved, the pH of the PAH solution is adjusted to a desired value.

Polyquat (PQ) Solutions

A solution of polyquat (PQ6-6) of formula (I), in which $R_1$, $R_2$, $R_3$, and $R_4$ are methyl groups, and A and B are hexamethylene groups, is prepared by dissolving a suitable amount of PQ6-6 in water to have a desired PQ6-6 concentration. Once dissolved, the pH of the PQ6-6 solution is adjusted to a desired value.

A solution of polyquat (PQ6-10) of formula (I), in which $R_1$, $R_2$, $R_3$, and $R_4$ are methyl radicals, and A and B are hexamethylene and decamethylene groups respectively, is prepared by dissolving a suitable amount of PQ6-10 in water to have a desired PQ6-6 concentration. Once dissolved, the pH of the PQ6-10 solution is adjusted to a desired value.

A solution of polyquat (PQ6-12) of formula (I), in which $R_1$, $R_2$, $R_3$, and $R_4$ are methyl groups, and A and B are hexamethylene and dodecamethylene respectively, is prepared by dissolving a suitable amount of PQ6-12 in water to have a desired PQ6-6 concentration. Once dissolved, the pH of the PQ6-12 solution is adjusted to a desired value.

A solution of poly(diallyldimethylammonium chloride) (PDADMAC) is prepared by dissolving a suitable amount of PDADMAC in water to have a desired PDADMAC concentration. Once dissolved, the pH of the PDADMAC solution is adjusted to a desired value.

EXAMPLE 2

Preparation of Contact lenses Having LbL Coatings

This example illustrates LbL coatings and several types of antimicrobial coatings which are formed on soft contact lenses made of a fluorosiloxane hydrogel material, lotrafilcon A.

(1) Coating Comprising Four and Half Bilayers:
PAA/PAH/PAA/PAH/PAA/PAH/PAA/PAH/PAA The contact lenses are dipped in a PAA solution (0.001 M, pH 2.5) for 30 min, rinsed with ultra-pure water, then dipped in a PAH solution (0.001 M, pH 7.5) for 5 minutes, rinsed with ultra-pure water for 1 minute. Three more bilayers are added by alternatively dipping in the solutions of PAA (0.001 M, pH 3.5) and PAH (0.002M, pH 7.5), with a rinse step in-between. The contact lenses with four bilayers of polyelectrolytes is dipped in the PAA solution (0.001 M, pH 3.5) and rinsed with ultra-pure water for 1 minute. The lenses are then packaged in saline and sterilized.

(2) Antimicrobial Coating Comprising 6 Bilayers:
PAA/PAH/PAA/PAH/PAA/PAH/PA/PAH/PAA/PAH/PAA/PQ6-12

The contact lenses are dipped in a PAA solution (0.001 M, pH 2.5) for 30 min, rinsed with ultra-pure water, then dipped in a PAH solution (0.001 M, pH 7.5) for 5 minutes, rinsed with ultra-pure water for 1 minute. Four more bilayers are added by alternatively dipping in the solutions of PAA (0.001 M, pH 3.5) and PAH (0.002M, pH 7.5), with a rinse step in-between. The contact lenses with five bilayers of polyelectrolytes is dipped in the PAA solution (0.001 M, pH 3.5) and rinsed with ultra-pure water for 1 minute. Finally, a capping layer of PQ6-12 is deposited by dipping lenses in a PQ6-12 solution (300 ppm, pH 6.5). The lenses are then packaged in saline and sterilized.

(3) Antimicrobial Coating Comprising 5 Bilayers:
PAA/PAH/PAA/PAH/PAA/PAH/PAA/PAH/PAA/PQ6-12

The contact lenses are dipped in a PAA solution (0.001 M, pH 2.5) for 30 minutes, dipped in a PAH solution (0.001 M, pH 4.5) for 5 minutes, rinsed with ultra-pure water, dipped in the PAA solution for 5 minutes, and rinsed with ultra-pure water. This procedure of dipping in an alternative fashion in the PAH and PAA solutions for 5 minutes and rinsing with water between two dipping steps is repeated until four and half bilayers with PAA as the outer layer are formed on the lenses. Then the lenses are dipped in a PQ6-12 solution (300 ppm, pH 5.1) for 5 minutes, followed by a water rinsing step. The lenses are then packaged in saline and sterilized.

(4) Antimicrobial Coating Comprising 5 Bilayers:
PAA/PAH/PAA/PAH/PAA/PAH/PA/PAH/PAA/PQ6-10

The contact lenses are dipped in a PAA solution (0.001 M, pH 2.5) for 30 minutes, then dipped in a PAH solution (0.001 M, pH 4.5) for 5 minutes, rinsed with ultra-pure water, then dipped in the PAA solution for 5 minutes, rinsed with ultra-pure water. This procedure of dipping in an alternative fashion in the PAH and PAA solutions for 5 minutes and rinsing with water between two dipping steps is repeated until four and half bilayers with PAA as the outer layer are formed on the lenses. Then the lenses are dipped in a PQ6-10 solution (300 ppm, pH 5.4) for 5 minutes, followed by water rinsing step. The lenses are then packaged in saline and sterilized.

(5) Antimicrobial Coating Comprising 5 Bilayers:
PAA/PAH/PAA/PAH/PAA/PAH/PAA/PAH/PAA/PQ6-6

The contact lenses are dipped in PAA (0.001 M, pH 2.5) for 30 min, then dipped in PAH (0.001 M, pH 4.5) for 5 min, rinsed with ultra-pure water, then dipped in PAA solution for 5 min, rinsed with ultra-pure water. This procedure of dipping in an alternative fashion in the PAH and PAA solutions for 5 minutes and rinsing with water between two dipping steps is repeated until four and half bilayers with PAA as the outer layer are formed on the lenses. Then the lenses are dipped in a PQ6-6 solution (300 ppm, pH 5.9) for 5 min, followed by water rinsing step. The lenses are then packaged in saline and sterilized.

(6) Antimicrobial Coating Comprising 6 Bilayers:
PAA/PAH/PAA/PQ6-1 O/PAA/PQ6-10/PAA/PQ6-10/PAA/PQ6-1 O/PAA/PQ6-10

The contact lenses are dipped in a PAA solution (0.001 M, pH 2.5) for 30 minutes, then dipped in a PAH solution (0.001 M, pH 4.5) for 5 min, and then rinsed with ultra-pure water. The lenses with the first bilayer formed thereon are then dipped in the PAA solution for 5 minutes, rinsed with ultra-pure water and then dipped in a PQ6-10 solution (300 ppm, pH 5.4) for 5 minutes, rinsed with water, and then dipped in the PAA solution and rinsed with water. The procedure comprising 5-minute dips in the PQ6-10 solution and in the PAA solution and water rinse steps between two dipping steps is repeated until a desired number of bilayers with either PAA or PQ6-10 as the outer layer are achieved. The lenses are then packaged in saline and sterilized.

(7) Antimicrobial Coating Comprising 6 Bilayers:
PAA/PAH/PAA/PDADMAC/PAA/PDADMAC/PAA/PDADMAC/PAA/PDADMAC/PAA/PDADMAC The contact lenses are first dipped in a PAA solution (0.001 M, pH 2.5) for 30 minutes, then dipped in a PDADMAC solution (0.001 M, pH 3.5) for 5 minutes, rinsed with ultra-pure water for 1 minute, then dipped in a PAA solution (0.001 M, pH 4.4) for 5 minutes, rinsed with ultra-pure water for 1 minute. This procedure of dipping in an alternative fashion in the PDADMAC and PAA solutions for 5 minutes and rinsing with water between two dipping steps is repeated until a desired number (from 5 to 10) of bilayers with PDADMAC as the outer layer are formed on the lenses. The lenses are then packaged in saline and sterilized.

It has been found that the pH of the polyquat solution used in the coating process can affect the quality of the antimicrobial coating, such as polyquat coverage. When the pH of the polyquat solution used in the coating process is low (e.g., less than 2.5) or high (e.g., higher than 7.0), delamination of the LbL coating can occur. Preferably, the pH of the polyquat solution used in the coating process is from about 3.0 to about 7.0, in order to obtain an antimicrobial coating with good polyquat coverage. It has also been found that there is no need for adjusting the pH of the polyquat solution used in the coating process. The unadjusted pH of the polyquat solution (300 ppm) generally is from about 5.0 to about 6.0, which is within the preferred pH range.

EXAMPLE 3

This example illustrates how to produce a covalently-attached antimicrobial coating on a contact lens made of lotrafilcon A, lotrafilcon B, or Balafilcon.

The contact lens is functionalized by spraying with or dipped into a diaziridine compound and then covalently coupling the diaziridine compound to the contact lens via a thermal process. Such functionalized lens is placed in an open dish containing a polyquat (PQ6-6, PQ6-10, PQ6-12, or PDADMAC) solution of about 10 µg/ml and irradiated with blue light for 30 minutes.

EXAMPLE 4

Coefficient of friction of a contact lens can be measured by a sled-on-block type of friction tester as follow. Under a certain load (e.g., about 3 grams), a contact lens is slid back and forth, at a prescribed speed, against a biologically relevant substrate and both the normal force (N) and the tangential force ($F_T$) are measured. The coefficient of friction of the contact lens is calculated based on the equation of $\mu = F_T/N$.

A preferred friction tester comprises: a stationary lens holder assembly, a biologically relevant substrate, a horizontally movable platform, and a plurality of force measuring means.

The stationary lens holder assembly preferably comprises an "A-shaped" holder bracket and a lens holder having a lens-supporting surface. The lens supporting surface of the lens holder has a convex curvature capable of accommodating the back (concave) surface of a contact lens. The lens holder is preferably held by a means in the center of the "A-shaped" holder bracket. The head end of the "A-shaped" stationary sample holder bracket is connected to a first force measuring means (e.g., a load cell from Transducer Techniques) by, for example, a Kevlar® fiber. The two foot end of the "A-shaped" holder bracket are connected to nylon string attached with two ½" steel extension springs. The first force measuring means and the steel extension springs are mounted to the frame of the tester.

The horizontally movable platform can be, for example, a table platform (x-table) which moves uniaxially at various speeds and accelerations. The x-table preferably has a dimension of 163 mm long and 19.1 mm wide and can provide a test area having about 140 mm long and about 14.7 mm wide. An example of the x-table is a Model 41 Linear Positioner which is powered by a ZETA Drive Compumotor (Parker Hannifin Corporation), which operates unidirectional at maximum velocities of 1800 mm/min and accelerations of 9000 mm/s².

The biologically relevant substrate can be any material and preferably is a powder-free surgical glove with Biogel® Coating" from Regent®. Preferably, the finger of the glove is cut into a single rectangular strip, and stretched and attached to the x-table by a physical means, for example, jumbo paper clips. Before testing, the substrate attached onto the x-table is lubricated with two drops of a desired lubricant, for example, ultra pure water or Softwear® saline (CIBA vision). Any air between the substrate and the x-table should be removed. The desired lubricant should be applied evenly on the substrate. The substrate should be even and consistent throughout.

Preferably, there are three force-measuring means, a first, a second and a third force-measuring means. Any suitable known force-measuring means can be used. An example is a 100-gram load cells from Transducer Techniques. The first force-measuring means is attached to the sample holder to measure tangential forces (friction forces, $F_T$) in two opposite directions. The second and third force-measuring means reside under the x-table to measure normal forces (N) in the downward direction. The other load cell Values outputted by the normal load cells are converted to grams by a Versatile Amplifier/Conditioner (Transducer Techniques).

Measurements of coefficient of friction is performed on the preferred friction tester as follows. A contact lens is placed on a lens holder with the back surface of the contact lens against the lens-supporting surface of the lens hold. The lens holder with the contact lens is assembled with the "A-shaped" holder bracket and then placed in contact with a desired lubricated substrate. This substrate is mounted to a horizontally movable table platform that is capable of moving uniaxially at various speeds and accelerations. About 3 grams of weight is loaded onto the lens holder. This load may represent the force pressed on a contact lens by a blink of eyelids. The tree force-measuring means (3 Load cells from Transducer Techniques) measure simultaneously the normal (N) and frictional ($F_T$) forces that are produced from the interaction between the contact lens and the substrate lubricated with a desired lubricant. Multiple data points are taken during a measurement of coefficient of friction of a contact lens. At each data point, the coefficient of Friction µ, is calculated as follows:

$$\mu = F_T/N$$

in which $F_T$ represent actual data reading at each point obtained by the first force measuring means after correcting for the preloading provided by the springs (tangential load cell) during sliding of the substrate against the contact lens and preferably has a unit of gram; N is the sum of $N_1$ and N2; N1 represents actual data reading at each point obtained by the second force-measuring means after correcting for any preloading by the test assembly (normal load cell#1) during sliding of substrate against the contact lens and preferably has a unit of gram; and $N_2$ represents actual data reading at each point obtained by the third force-measuring means after correcting for any preloading by the test assembly (normal load cell#2) during sliding of substrate against the contact lens and has preferably a unit of gram. The average ($\mu_{Ave}$) of all µ's at every data point will be used to represent the value of coefficient of friction of a contact lens.

More preferably, the friction tester further comprises a computer system that controls the tester, collects readings of the normal and tangential forces simultaneously as the biologically-relevant substrate interacts with contact lens, calculates coefficient of friction, and records and charts the forces ($F_T$ and N) and the coefficient of friction (µ) at each data point during testing.

EXAMPLE 5

Antimicrobial Activity of Contact Lenses Having One or More Layer of Polyquats Contact lenses having an LbL coating of PAA/PAH/PAA/PAH/PAA/PAH/PAA/PAH/PAA (4½ bilayers) and a capped layer of polyquat are tested for antimicrobial activity against *Pseudomonas aeruginosa* #3, which is isolated from a corneal ulcer.

Effects of pH of polyquat coating solutions on antimicrobial activity are studied. The contact lenses are prepared as described in Example 2. The pHs of the PQ6-12 solution used in forming the capping layer of polyquat are from 2.5 to 6.5. The contact lenses are incubated for three days with *Pseudomonas aeruginosa* GSU #3 suspended in PBS. The inoculum size is $1.0 \times 10^4$ cfu/ml. No significant difference in antimicrobial activity of contact lenses is observed for those solution having a pH of from 3.0 to 6.5. For further antimicrobial activity assays, the pH of the polyquat solution is within 3.0 to 6.5.

The contact lenses are prepared as described in Example 2. The pHs of the PQ6-12 solution used in forming the capping layer of polyquat are 5.5 and 6.5 respectively. The contact lenses are soaked in a cell suspension of $1\times10^3$ of *Pseudomonas aeruginosa* GSU #3 at 37° C. for 20 hours. Lenses are removed from the cell suspension and immediately soaked/rinsed in 250 ml of PBS (Dulbecco). The rinsing step is repeated for 3 consecutive times. After rinsing with PBS, each lens is placed on a petri dish. Molten agar is poured into the petri dish containing one lens. The agar dish containing the lens is inverted and incubated at about 30° C. to 35° C. for about 24 to 48 hours.

As a positive control, contact lenses with coatings, each having four and half bilayers PAA/PAH/PAA/PAH/PAA/PAH/PAA, are tested for antimicrobial activity against *Pseudomonas aeruginosa* GSU #3 according to the above-described procedures.

As a negative control, contact lenses with coatings, each having four and half bilayers PAA/PAH/PAA/PAH/PAA/PAH/PAA, are soaked in bleach for 30 minutes and then rinsed with PBS. The lenses are then inoculated with *Pseudomonas aeruginosa* GSU #3 and antimicrobial activity is tested according to the above-described procedures.

Results of antimicrobial activity assays are shown in Table 1.

TABLE 1

|  | Colonies on the lenses | | |
| --- | --- | --- | --- |
|  | No. 1 lens | No. 2 lens | No. 3 lens |
| Lens coated w/PQ6-12[1] | 3 | 1 | 0 |
| Lens coated w/PQ6-12[2] | 0 | 2 | 2 |
| Positive control | ++++* | ++++* | ++++* |
| Negative control | none | none | none |

*Colonies are observed all over the lens. Confluent growth is also observed on the plate.
[1]pH of the PQ6-12 coating solution is 5.5.
[2]pH of the PQ6-12 coating solution is 6.5.

Surface antimicrobial activities of contact lenses with antimicrobial coating are also assayed. Contact lenses are prepared as described in Example 2 and each contains an antimicrobial coating of PAA/PAH/PAA/PAH/PAA/PAH/PAA/PAH/PAA (4½ bilayers) and a capped layer of polyquat (PQ6-6, PQ6-10, or PQ6-12). The pHs of the polyquat solutions (300 ppm) used in forming the capping layer of polyquat are unadjusted and from about 5.0 to about 6.0. Two types of control contact lenses are used. Each of the first type of control contact lenses comprises an LbL coating having 4½ bilayers, PAA/PAH/PAA/PAH/PAA/PAH/PAA/PAH/PAA. The second type of control contact lenses is plasma-coated contact lenses. The plasma-coated contact lenses are prepared in substantial accordance with teachings in PCT Publication No. WO 96/31792 to Nicolson et al. All contact lenses are made of lotrafilcon A. 200 microliter of inoculum solution ($10^4$/CFU of *Pseudomonas aeruginosa* GSU #3) is placed on the test lenses, incubated for ~18 hours at 25° C. A portion of the inoculum is extracted, serially diluted and plated out on agar plates for comparison to determine the microbial load of each lens type. At 24 hours, colony counts are taken from each lens. Results are shown in Table 2.

TABLE 2

| Contact lenses | cfu recovered from the surface of the lens* |
| --- | --- |
| Control 1 (4½ bilayers) | TNTC# (solid lawn of bacteria) |
| Control 2 (plasma-coating) | TNTC# (solid lawn of bacteria) |
| A capping LbL layer of PQ6-6 | 377 |
| A capping LbL layer of PQ6-10 | 0 |
| A capping LbL layer of PQ6-12 | 0 |

*Values averaged over three tested contact lenses.
TNTC represents "too numerous to count".

Results in Table 2 indicate the antimicrobial activity on the surface of the contact lenses having antimicrobial coatings. The antimicrobial coatings with a capping layer of PQ6-12 or PQ6-10 show relatively high antimicrobial efficacy. The antimicrobial coating with a capping layer of PQ6-6 shows antimicrobial activity but less than the activity demonstrated by the other antimicrobial coatings containing PQ6-12 or PQ6-10.

Contact lenses having a coating comprising covalently attached PQ6-12 are tested for antimicrobial activity against *Staphylococcus aureus* (ATCC 6538). The contact lenses are prepared as described in Example 3. Lenses to which polyquats are covalently attached are placed in 0.5 ml of $1\times10^4$ cfu Staphylococcus aureus (ATCC 6538) in an artificial tear fluid at 37° C. with shaking for 24 hours. The composition and preparation of the artificial tear fluid is described by Mirejovsky et al. in Optom. Vis. Sci. 68: 858-864 (1991), herein incorporated by reference. After 24 hours, the contact lenses are removed and rinsed 3 times in 250 ml of phosphate buffered saline (PBS) and then placed in a vial containing 10 ml of Dulbecco's PBS, sonicated for 6 minutes followed by vortexing for 1-2 minutes. The effluent from each lens is serially diluted, plated out and incubated inverted at 35° C. Colonies are counted after about 24 to 48 hours of incubation. As a control, contact lenses made of the same material (lotrafilcon A) are functionalized with a diaziridine compound. These control contact lenses are also tested using the identical antimicrobial activity assay procedure. Number of cfu recovered from the control contact lenses is about $1.9\times10^4$. Number of cfu recovered from the contact lenses having a coating comprising covalently attached PQ6-12 is undetectable.

EXAMPLE 6

Surface Properties of Contact Lenses Having Antimicrobial Coatings

The contact angle generally measures the surface hydrophilicity of a contact lens. In particular, a low contact angle corresponds to more hydrophilic surface. Average contact angles (Sessile Drop) of contact lenses are measured using a VCA 2500 XE contact angle measurement device from AST, Inc., located in Boston, Mass. The averaged contact angle of a contact lens, which is made of lotrafilcon A and without any coating (LbL or plasma), is about 112 degree. When such contact lens has a surface modification through LbL coating or plasma coating, the averaged contact angle is decreased generally to less than 70 degrees. Where a contact lens having an antimicrobial coating comprising one or more layer of polyquat, the averaged contact angle is determined to be from about 30 degree to about 65 degrees.

Coefficient of friction (COF) may be one of parameters that measure the easiness of the on-eye movement of a contact lens. High coefficient of friction may increase the likelihood of damaging mechanically the ocular epithelia. The COF is measured as described in Example 4. Multiple lenses are measured to obtain the averaged COF. A contact lens without any surface modification (i.e., plasma treatment or LbL coating), which is made of lotrafilcon A, has an averaged coefficient of friction of about 1.8. A contact lens having an LbL or antimicrobial coating has a smaller averaged COF (Table 3).

TABLE 3

| LbL or Antimicrobial Coating on a Contact lens (lotrafilcon A) | COF |
|---|---|
| PAA/PAH/PAA/PAH/PAA/PAH/PAA/PAH/PAA | $1.32 \pm 0.12^1$ |
| PAA/PAH/PAA/PAH/PAA/PAH/PAA/PAH/PAA/PQ6-6 | $1.29 \pm 0.11^1$ |
| PAA/PAH/PAA/PAH/PAA/PAH/PAA/PAH/PAA/PQ6-6/PAA | $1.11 \pm 0.13^1$ |
| PAA/PAH/PAA/PAH/PAA/PAH/PAA/PAH/PAA/PQ6-10 | $1.41 \pm 0.02^2$ |
| PAA/Q6-6/PAA/Q6-6/PAA/Q6-6/PAA/Q6-6/PAA | $1.31 \pm 0.03^2$ |

[1] Averaged value based on measurements of 10 lenses.
[2] Averaged value based on measurements of 3 lenses.

It has been found that the desirable bulk properties of the lens, such as oxygen permeability, ion permeability, and optical properties are not significantly affected by the antimicrobial coating comprising one or more layer of polyquat (PQ6-6, PQ6-10 or PQ6-12) on the lens. The ion permeability of a contact lens measures the ability of ions to diffuse through the contact lens. The Dk value of a contact lens is generally a measure of the ability of a gas, such as oxygen, to diffuse through a contact lens. A more detailed description of the ion permeability and Dk value can be obtained by reference to U.S. Pat. No. 5,760,100.

EXAMPLE 7

The potency of polyquat against *Pseudomonas aeruginosa* GSU #3 is tested at a concentration of 0.5, 1, 5 and 10 ppm. The inoculum is between $5 \times 10^5$-$1 \times 10^6$ cfu/ml. There is more than 3-log reduction demonstrated by the biocidal assay. Minimum inhibition concentrations (MICs) are determined and shown in Table 4.

Cytotoxicity of polyquat is also evaluated according to the USP Elution Test ("Biological Reactivity Tests, In-Vitro: Elution Test", The United States Pharmacopeial Convention, Inc.). Cell cultures, L929 mammalian fibroblasts (ATCC cell line CCL1, NCTC clone 929), are grown to a near confluent monolayer in 6 well plates (individual wells are 35 mm diameter). A polyquat solution is diluted with serum-supplemented cell culture medium at 25% test solution concentration. The serum-supplemented cell culture medium is prepared by mixing 1000 mL Eagle's sterile minimum essential medium (MEM), 100 mL serum, 10 ml L-glutamine solution and antibiotic-antimycotic solution. Each culture is examined microscopically after 48 hours using trypan blue for the presence of morphological changes, reduction in cell density or cell lysis induced by the polyquat solution. The results of cytotoxicity assay are shown in Table 4.

TABLE 4

| Polyquat | Potency (MIC) | Cytotoxicity |
|---|---|---|
| PQ6-6 | 2-10 ppm | Passed at 50 ppm |
| PQ6-10 | 0.5 ppm | Passed at 25 ppm |
| PQ6-12 | 0.5 ppm | Failed at 25 ppm |

Contact lenses (made of lotrafilcon A, having an LbL coating of PAA/PAH/PAA/PAH/PAA/PAH/PAA/PAH/PAA and contact lenses (lotrafilcon A) having an antimicrobial coating of PAA/PAH/PAA/PAH/PAA/PAH/PAA/PAH/PAA/PQ6-10 are evaluated for cytotoxicity according to the L929 Cell Growth Assay (Coulter Counter Method). For this assay, cells grown under controlled conditions are monitored for their ability to survive and grow following initial exposure and incubation with extracts of lenses. The lenses are rinsed with 10 mL of 0.9% Sodium Chloride Injection, USP, and then extracted using 20 lenses in 10 mL of 0.9% Sodium Chloride Injection, USP, at $121\pm2°$ C. for 1 hour. The extract is diluted with growth media (serum-supplemented MEM) to 50% extract concentration and is applied to the L929 cells. Cell counts are determined upon initiation of the test (Initial, Time=0) and after 72 hours with and without addition of test sample (lens extract). The calculation of the percent inhibition of cell growth induced by the extract is determined by comparison of cell growth for the control cultures to the test cultures. This test evaluated the ability of cells to survive a toxic insult as measured by retention of proliferative ability. Results are shown in Table 5.

TABLE 5

| Tests and Control Sample description | % inhibition |
|---|---|
| Test Samples: | |
| Contact lenses (lotrafilcon A) with LbL coatings | 12 |
| Contact lenses (lotrafilcon A) with antimicrobial coatings | 10 |
| Control Samples: | |
| Sodium Chloride Injection (0.9% NaCl) (negative control) | 0 |
| 5% ethanol solution (w/PBS) (positive control) | 100 |

The results in Table 5 indicate that there is no significant difference between contact 20 lenses having LbL coatings and contact lenses having antimicrobial coatings. Both types of contact lenses can be considered non-cytotoxic since the growth inhibition is less than 30%, which is the threshold for a cytotoxic response in the eye.

EXAMPLE 8

In vivo Toxicity Tests

In vivo toxicity of antimicrobial coatings on contact lenses is tested by trying these contact lenses with antimicrobial coatings on the eyes of New Zealand white rabbits. Contact lenses, designed to accommodate rabbit eyes and made of lotrafilcon A, were manufactured. An antimicrobial coating comprising 4½ bilayer (PAA/PAH/PAA/PAH/PAA/PAH/PAA/PAH/PAA) and a capping layer of PQ6-12 is applied onto each lens in accordance with the procedure described in Example 2. The eyes of New Zealand white rabbits are examined after they wear the contact lenses with the antimicrobial coatings on eye for 7 days and 6 nights. Microscopic evaluation of the ocular tissue sections reveals no evidence of corneal or conjunctival damage in any of the test or control eyes.

Intra-Stromal Corneal Implantation Test

Control lenses (made of lotrafilcon A and with an LbL coating comprising 4½ bilayer, PAA/PAH/PAA/PAH/PA/PAH/PAA/PAH/PAA), and segments of contact lenses with antimicrobial coatings each comprising a capping layer of PQ6-12 and 4½ bilayer (PAA/PAH/PAA/PAH/PAA/PAH/PAA/PAH/PAA) are surgically implanted into corneal stroma of New Zealand white rabbits to evaluate toxicity reactions. The lenses are inserted into the eye to mid-depth in the corneal stroma. All eyes are harvested for histopathology after one week of wear. There are no signs of inflammation.

Intramuscular Implantation Test

New Zealand white rabbits are implanted with strips of the antimicrobial contact lenses and the control lenses on the dorsal side for a period of seven days. The animals are observed daily to insure proper healing of the implant sites and for clinical sites of toxicity. The implanted sites are excised from the rabbits and examined with macroscopic observations and histopathology analysis. None of the test animals exhibits signs of toxicity over the course of the study. Microscopic evaluation of the test article sites indicates no signs of inflammation, fibrosis, hemorrhage, necrosis of degeneration as compared to the negative or to the predicate control article sites.

All results shown in the above examples demonstrate that the antimicrobial coatings on contact lenses have a high antimicrobial efficacy, a low toxicity, low coefficient of friction (with an averaged value of less than 1.4), and increased hydrophilicity (characterized by an averaged contact angle of less than 80 degree) while maintaining the desired bulk properties such as oxygen permeability and ion permeability of lens material. Such lenses are useful as extended-wear contact lenses.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

What is claimed is:

1. A medical device, comprising a core material and an antimicrobial surface coating, wherein said antimicrobial surface coating is an LbL coating obtained by using a layer-by-layer deposition technique and comprises at least one polyanionic-polyquat bilayer composed of one layer of a polyanionic material and one layer of the polyquat of formula (1),

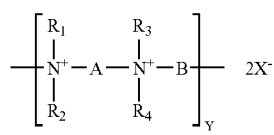

wherein $R_1$, $R_2$, $R_3$ and $R_4$, independently of one another, are $C_1$-$C_{10}$ hydrocarbon radicals, wherein A and B, independently of one another, are n-alkylene groups having 3 to 15 carbon atoms or n-alkylene groups having 3 to 15 carbon atoms and one or more hydroxyl groups, wherein the index y is a number from about 10 to 500, wherein X is chlorine, bromine, or iodine, wherein said antimicrobial surface coating imparts to said medical device the following surface properties:

(a) a low coefficient of friction with a averaged value of less than 1.55, and (b) hydrophilicity characterized by having an averaged contact angle of less than 80 degree, wherein the value of the averaged contact angle is obtained by averaging measurements of at least 3 individual medical devices, and using Sessile Drop test method.

wherein the polyanionic material is selected from the group consisting of polyacrylic acid, polymethacrylic acid, and mixtures thereof.

2. A medical device of claim 1, wherein said antimicrobial surface coating comprises one or more layers of polyquat of formula (I) in which one of A and B is hexamethylene radical (—$CH_2CH_2CH_2CH_2CH_2CH_2$—) and the respective other one is an n-alkylene group having 6 to 12 carbon atoms.

3. A medical device of claim 1, wherein the medical device is an ophthalmic lens.

4. An ophthalmic lens of claim 3, wherein the ophthalmic lens is a contact lens.

5. A contact lens of claim 4, wherein the antimicrobial surface coating comprises a capping layer of the polyquat of formula (I).

6. A contact lens of claim 4, wherein the antimicrobial surface coating further comprises at least one polyelectrolyte bilayer which is composed of one layer of the polyanionic material and one layer of a polycationic material.

7. A contact lens of claim 6, wherein the polycationic material is selected from the group consisting of poly(allylamine hydrochloride), poly(ethyleneimine), poly(vynylbenzyltriamethylamine), polyaniline, polypyrrole, poly(pyridinium acetylene), and mixtures thereof.

8. A contact lens of claim 4, wherein said core material is a hydrogel.

9. A contact lens of claim 8, wherein said hydrogel is a siloxane-containing polymer.

* * * * *